United States Patent
Kanaumi et al.

(10) Patent No.: US 11,202,581 B2
(45) Date of Patent: Dec. 21, 2021

(54) BLOOD FLOW SENSOR AND BLOOD FLOW MEASUREMENT DEVICE

(71) Applicant: NS Materials Inc., Fukuoka (JP)

(72) Inventors: Eiichi Kanaumi, Fukuoka (JP); Hiroaki Ogino, Fukuoka (JP); Tomoyuki Ogawa, Fukuoka (JP)

(73) Assignee: NS Materials Inc.

( * ) Notice: Subject to any disclaimer, the term of this patent is extended or adjusted under 35 U.S.C. 154(b) by 452 days.

(21) Appl. No.: 16/080,052

(22) PCT Filed: Mar. 3, 2017

(86) PCT No.: PCT/JP2017/008499
§ 371 (c)(1),
(2) Date: Aug. 27, 2018

(87) PCT Pub. No.: WO2017/150708
PCT Pub. Date: Sep. 8, 2017

(65) Prior Publication Data
US 2019/0014995 A1  Jan. 17, 2019

(30) Foreign Application Priority Data
Mar. 4, 2016 (JP) .............................. JP2016-041704

(51) Int. Cl.
*A61B 5/026* (2006.01)
*A61B 5/00* (2006.01)
*A61B 5/0285* (2006.01)

(52) U.S. Cl.
CPC .......... *A61B 5/0261* (2013.01); *A61B 5/0285* (2013.01); *A61B 5/6843* (2013.01); *A61B 5/6885* (2013.01); *A61B 5/746* (2013.01)

(58) Field of Classification Search
None
See application file for complete search history.

(56) References Cited

U.S. PATENT DOCUMENTS

2010/0087717 A1  4/2010  Onoe
2016/0310023 A1* 10/2016  Chachisvilis ............ A61B 8/06

FOREIGN PATENT DOCUMENTS

| GB | 2132483 A | 2/1986 |
| GN | 101371780 A | 2/2009 |

(Continued)

OTHER PUBLICATIONS

Song et al. Design of a solenoid actuator with a magnetic plunger for miniaturized segment robots, appl. sci. 2015, 5, 505-607 (Year: 2015).*

(Continued)

*Primary Examiner* — Pascal M Bui Pho
*Assistant Examiner* — Marjan Saboktakin
(74) *Attorney, Agent, or Firm* — Jordan and Koda, PLLC

(57) ABSTRACT

To provide a blood flow sensor in which a fluctuation of measurement results is suppressed during measurement of the blood flow volume. A probe portion is provided with a sensor portion which has a laser diode generating laser light, a photodiode receiving light, and a sensor housing having a contact surface contacting a subject and which irradiates a subject with the laser light generated by the laser diode through the contact surface, receives reflected light from the subject in the photodiode, and outputs a signal relating to the received light amount, a holding portion holding the sensor housing so as to be movable in an up-and-down direction crossing the contact surface, and a coil spring absorbing and transmitting external force applied to the holding portion to the sensor portion.

5 Claims, 10 Drawing Sheets

(56) References Cited

FOREIGN PATENT DOCUMENTS

| | | | |
|---|---|---|---|
| JP | 54-59786 | U | 4/1979 |
| JP | 6397146 | A | 4/1988 |
| JP | 08299292 | * | 1/1995 |
| JP | 08299292 | A | 11/1996 |
| JP | 10118039 | A | 5/1998 |
| JP | 2007244600 | A | 9/2007 |
| WO | 2015/085240 | A1 | 5/2015 |

OTHER PUBLICATIONS

Copy from http://nano-micro.mech.kyushu-u-ac.jp/detail.血流量.pdf (with english translation of excerpts).

* cited by examiner

BLOOD FLOW SENSOR AND BLOOD FLOW MEASUREMENT DEVICE

TECHNICAL FIELD BACKGROUND OF THE INVENTION

The present invention relates to a blood flow sensor and a blood flow measurement device measuring the blood flow volume using the Doppler shift of light.

Heretofore, a blood flow sensor measuring the blood flow volume of a blood vessel is known. For example, Patent Document 1 describes a blood flow sensor using laser light. In this blood flow sensor, a probe is brought into contact with biological tissues (for example, skin of a subject) to noninvasively measure the blood flow volume. Specifically, laser light is emitted to the biological tissues from the probe, reflected light from erythrocytes in a blood vessel is received with the probe, and then the reflected light is analyzed in a blood flowmeter body, whereby the blood flow volume is measured.

Moreover, Patent Document 2 discloses a configuration in which a finger pressure equalization means is provided in a pulse wave detector detecting pulse waves based on blood flow volume changes. The finger pressure equalization means has a pressing member against which the fingertip of a subject is pressed and a spring energizing the pressing member toward a finger, in which the pressure applied to a blood vessel by the pressing member is substantially equalized, so that influence on the blood flow is suppressed.

Moreover, Non-Patent Document 1 describes a small blood flow sensor using no optical fibers. The blood flow sensor is attached to the surface of a sensor probe. The blood flow is measured by pressing the surface of the sensor probe against a subject or sticking the surface of the sensor probe to a subject with a double-sided tape.

CITATION LIST

Patent Documents

Patent Document 1: Japanese Unexamined Patent Application Publication No. 10-118039
Patent Document 2: Japanese Unexamined Patent Application Publication No. 2007-244600

Non-Patent Document

Non-Patent Document 1:
http://nano-micro.mech.kyushu-u.ac.jp/detail_Ketsuryuryo (blood flow volume).pdf

SUMMARY OF INVENTION

In the blood flow sensor performing the measurement by bringing the blood flow sensor into contact with the skin, the contact pressure of the blood flow sensor to the skin may fluctuate during the measurement. When the contact pressure of the blood flow sensor fluctuates, the blood flow changes, so that the measurement result fluctuates.

The present invention has been made in view of the above-described circumstances. It is an object of the present invention to provide a blood flow sensor in which the fluctuation of measurement results is suppressed during the measurement of the blood flow volume.

(1) A blood flow sensor according to the present invention has a sensor portion which has a laser element generating laser light, a light receiving element receiving light, and a housing having a contact surface contacting a subject and which irradiates the subject with the laser light generated by the laser element through the contact surface, receives reflected light from the subject in the light receiving element, and outputs a signal relating to the received light amount, a holding portion holding the housing so as to be movable in a direction crossing the contact surface, and a transmission portion absorbing and transmitting external force applied to the holding portion to the sensor portion.

According to the above-described configuration, the blood flow volume is measured in the state where the contact surface of the housing in the sensor portion is in contact with the subject (for example, skin of a human body). The sensor portion is movably held in the holding portion and the external force applied to the holding portion is absorbed and transmitted to the sensor portion by the transmission portion. Therefore, when the external force is applied to the holding portion, changes of the contact pressure of the contact surface to the skin are suppressed. Thus, the fluctuation of the blood flow volume of the subject is suppressed during the measurement.

(2) Preferably, the transmission portion is an elastic member connecting the holding portion and the sensor portion.

According to the above-described configuration, when external force is applied to the holding portion, changes of the contact pressure of the contact surface to the subject are suppressed by a simple configuration.

(3) Preferably, the elastic member is a spring.

According to the above-described configuration, when external force is applied to the holding portion, changes of the contact pressure of the contact surface to the subject are more effectively suppressed.

(4) A blood flow measurement device according to the present invention has the blood flow sensor according to any one of claims 1 to 6, a calculation portion calculating the blood flow volume based on a signal output by the light receiving element, and a display portion displaying a calculation result by the calculation portion.

(5) The blood flow sensor further has a pressure sensor detecting the pressure applied to the contact surface from the subject.

(6) Preferably, a storage portion is further provided. The calculation portion acquires the pressure detected by the pressure sensor at each predetermined timing stored in the storage portion, performs the calculation corresponding to the timing, and does not perform the calculation corresponding to the timing at which the pressure is acquired in accordance with the fact that the acquired pressure is not within a predetermined range previously stored in the storage portion.

According to the above-described configuration, a calculation is not performed when the contact pressure of the contact surface to the subject is out of the predetermined range. Therefore, the display of calculation results with low reliability on a display portion is avoided.

(7) The calculation portion performs the calculation corresponding to the timing at which the pressure is acquired in accordance with the fact that the acquired pressure is within the predetermined range previously stored in the storage portion.

According to the above-described configuration, even in a case where the pressure detected by the pressure sensor is out of the predetermined range, when the pressure detected by the pressure sensor falls under the predetermined range again, a calculation is performed without explicit giving of a direction of starting the calculation to the calculation portion by a measurement person.

(8) The calculation portion performs the calculation by the predetermined number of times stored in the storage portion or more, calculates an average value of results of the predetermined number of times or more of the calculations, and then displays the average value as the calculation result on the display portion.

According to the above-described configuration, a more reliable calculation result is displayed on the display portion.

(9) A blood flow sensor according to the present invention has an optical sensor portion which has a contact surface contacting a subject and which receives reflected light from the subject through the contact surface, and then outputs a signal, a holding portion holding the optical sensor portion so as to be movable in movement directions crossing the contact surface, a first elastic body energizing the optical sensor portion in a first direction where the contact surface goes away from the holding portion among the movement directions, a moving member energized in the first direction by the first elastic body, and a pressure sensor abutting on the moving member by movement of the moving member in a second direction opposite to the first direction against energization force of the first elastic body, detecting the abutment, and then outputting a signal.

According to the above-described configuration, when the contact surface of the optical sensor portion is brought into contact with the subject in a state where the holding portion is held by a user, the moving member moves in the second direction to abut on the pressure sensor.

(10) Preferably, the blood flow sensor further has a second elastic body which is located between the optical sensor portion and the moving member and can be elastically compressed and deformed in the movement directions, in which the first elastic body is located between the moving member and the pressure sensor, the optical sensor portion can abut on the moving member by moving in the second direction against energization force of the second elastic body, and first energization force of the first elastic body in a state where the moving member and the pressure sensor abut on each other is lower than second energization force of the second elastic body in a state where the optical sensor portion and the moving member abut on each other.

According to the above-described configuration, when the contact surface of the optical sensor portion is brought into contact with the subject in a state where the holding portion is held by a user, the first elastic body is compressed, so that the moving member and the pressure sensor abut on each other. Further, when the contact surface of the optical sensor portion is strongly pressed against the subject, the second elastic body is compressed, so that the optical sensor portion and the moving member abut on each other. Thus, force applied to the optical sensor portion is directly transmitted to the pressure sensor.

(11) Preferably, in an equilibrium in which the first elastic body and the second elastic body are balanced, a first distance along the movement directions between the moving member and the pressure sensor is shorter than a second distance along the movement directions between the optical sensor portion and the moving member.

According to the above-described configuration, the moving member and the pressure sensor abut on each other with a relatively short distance. Moreover, the distance until the optical sensor portion and the moving member abut on each other is relatively long in the state where the moving member and the pressure sensor abut on each other, and therefore the range of a relative distance between the optical sensor portion and the moving member where the blood flow volume can be measured can be lengthened.

(12) Preferably, the optical sensor portion has a laser element generating laser light, a light receiving element receiving light, and a housing having a contact surface contacting a subject and irradiates the subject with the laser light generated by the laser element through the contact surface, receives reflected light from the subject in the light receiving element, and then outputs a signal relating to the received light amount.

(13) A blood flow volume measuring device according to the present invention has the above-described blood flow sensor, a calculation portion calculating the blood flow volume based on an output of the optical sensor portion according to an output of the pressure sensor, a storage portion storing a first threshold value and a second threshold value, and a warning portion issuing a warning, in which the calculation portion calculates the blood flow volume based on the output of the optical sensor portion on condition that the output of the pressure sensor is larger than the first threshold value and causes the warning portion to issue a warning on condition that the output of the pressure sensor is larger than the second threshold value.

According to the above-described configuration, when a proper load exceeding the first threshold value is given to the contact surface of the optical sensor portion, the calculation portion calculates the blood flow volume and when an excessive load exceeding the second threshold value is given to the contact surface of the optical sensor portion, a warning is issued.

According to the present invention, external force applied to the holding portion is absorbed and transmitted to the sensor portion, whereby a fluctuation of the contact pressure is suppressed, and therefore a fluctuation of measurement results is suppressed during the measurement.

DESCRIPTION OF EMBODIMENTS

Figure 1:
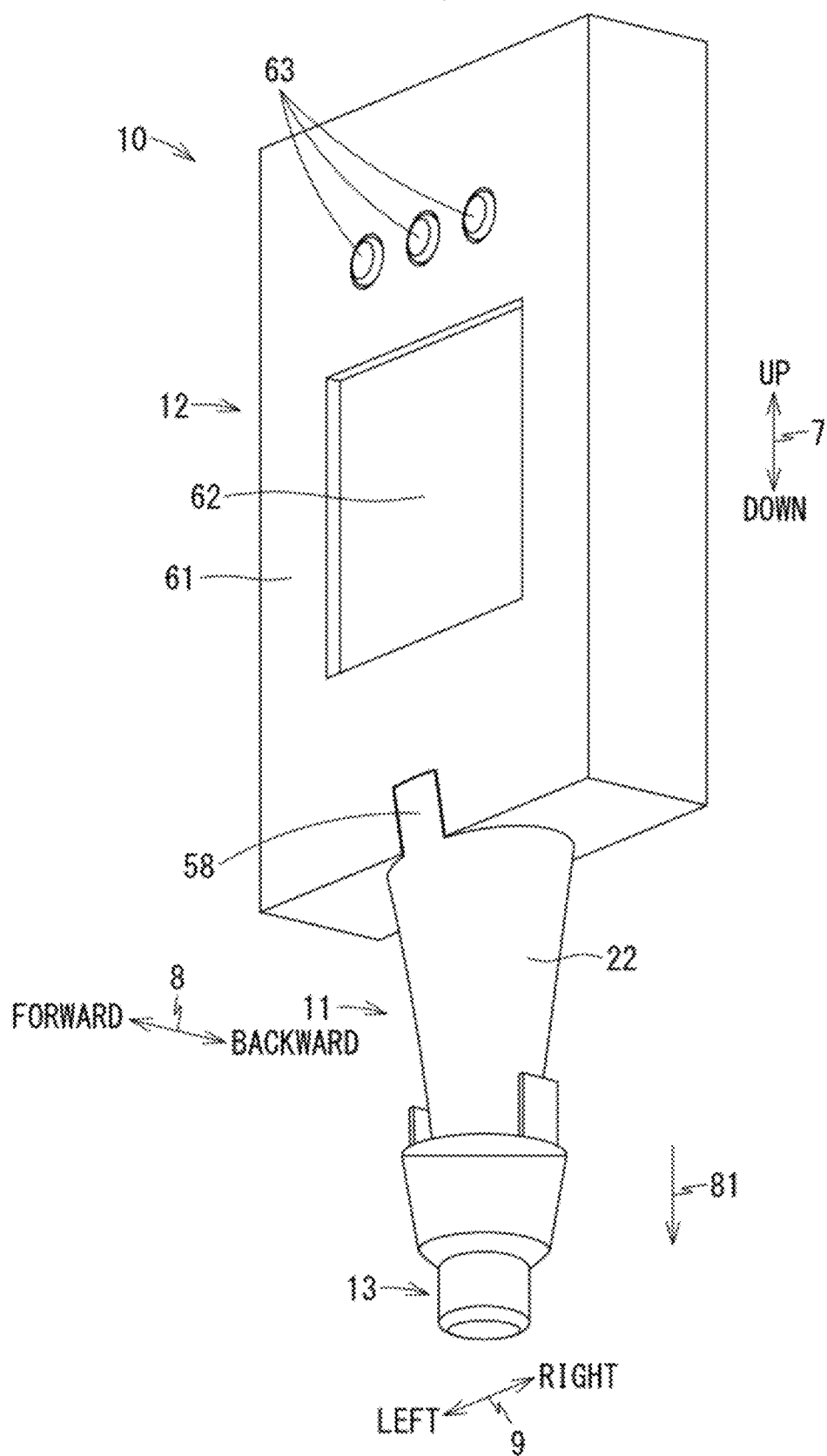
FIG. 1 is a perspective view illustrating the appearance of a blood flow measurement device 10.

Hereinafter, preferable embodiments of the present invention are described referring to the drawings as appropriate. It is a matter of course that the embodiments described below are merely examples of the present invention and the embodiments of the present invention can be altered as appropriate without deviating from the gist of the present invention. In the following description, an up-and-down direction 7 (example of the direction crossing a contact surface) is defined with a direction (pressing direction 82) in which a probe portion 11 is located with respect to a body portion 12 as a downward direction, a forward and backward direction 8 is defined with the side where a display portion 62 is provided as the front, and a left-and-right direction 9 is defined when the blood flow measurement device 10 is viewed from the front.

First Embodiment

The blood flow measurement device 10 measures the blood flow volume by the LDF (abbreviation for Laser Doppler Flowmetry) method. The LDP method is a method for calculating the blood flow volume from information based on the Doppler shift of light scattered by erythrocytes when biological tissues are irradiated with laser light.

As illustrated in FIG. 1, the blood flow measurement device 10 has the probe portion 11 (example of the blood flow sensor) and the body portion 12.

Figure 2:
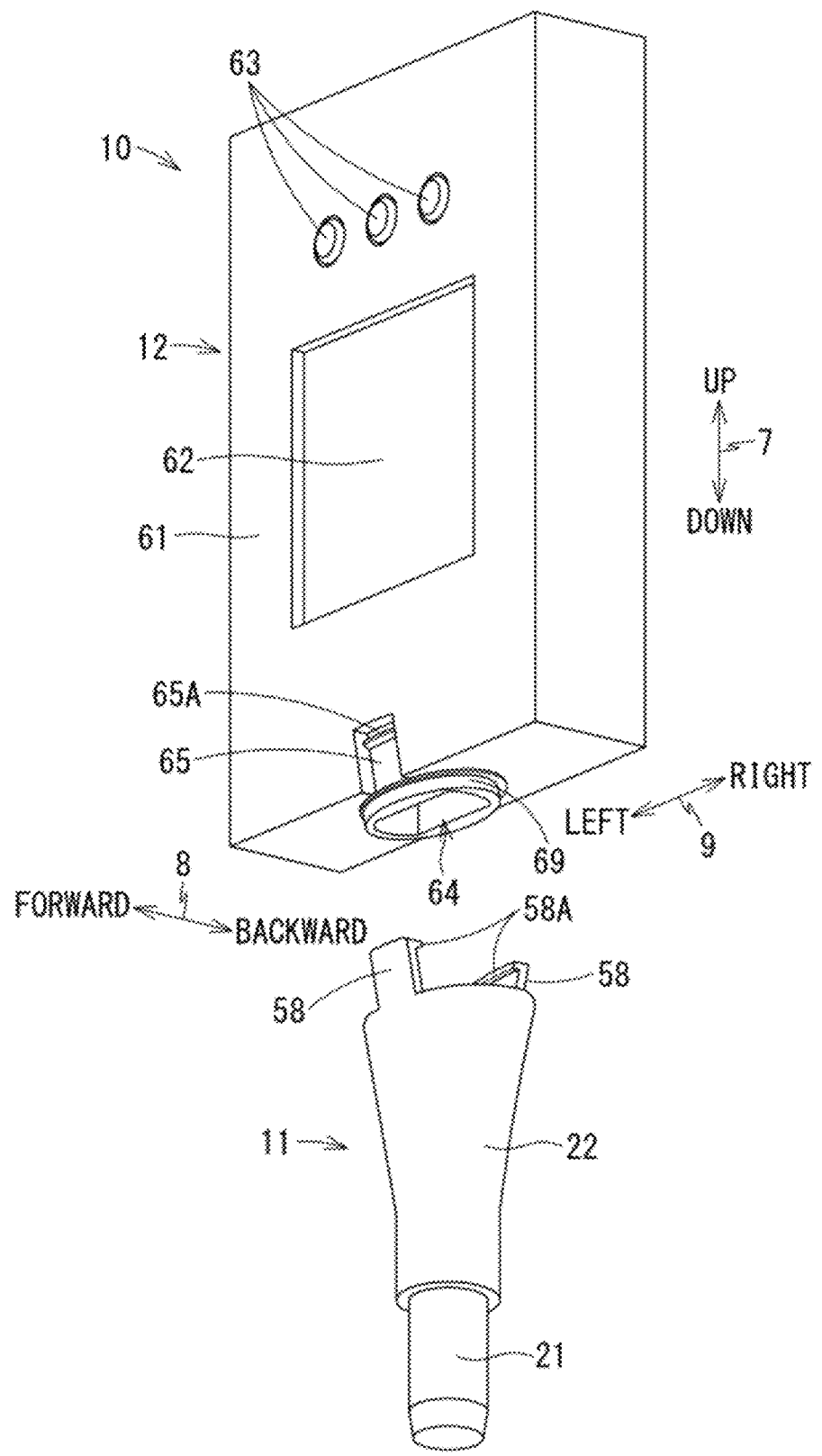
FIG. 2 is a perspective view illustrating the blood flow measurement device 10 in a state where a probe portion 11 is removed from a body portion 12.

As illustrated in FIG. 2, the probe portion 11 is configured so as to be attachable to and detachable from the body portion 12. Specifically, the probe portion 11 has a pair of engagement portions 58 and a protrusion portion 57 (see FIG. 3) as described later and the body portion 12 has a pair of engagement portions 65 engaging with the pair of engagement portions 58 of the probe portion 11 and a recessed portion 69 into which the protrusion portion 57 of the probe portion 11 is fitted as described later. In a process in which the probe portion 11 is attached to the body portion 12, an upper end portion of a holding portion 22 and the pair of engagement portions 58 are elastically deformed so as to extend outward, and then the protrusion portion 57 and projections 58A of the engagement portions 58 of the holding portion 22 are fitted into the recessed portion 69 and recessed portions 65A of the engagement portions 65 of the body portion 12, respectively. In a process in which the probe portion 11 is pulled out from the body portion 12, the upper end portion of the holding portion 22 and the pair of engagement portions 58 are elastically deformed so as to extend outward, and then the protrusion portion 57 and the projections 58A of the engagement portions 58 of the holding portion 22 are separated from the recessed portion 69 and the recessed portions 65A of the engagement portions 65 of the body portion 12, respectively. Thus, the probe portion 11 is attachable to and detachable from the body portion 12.

Figure 3:
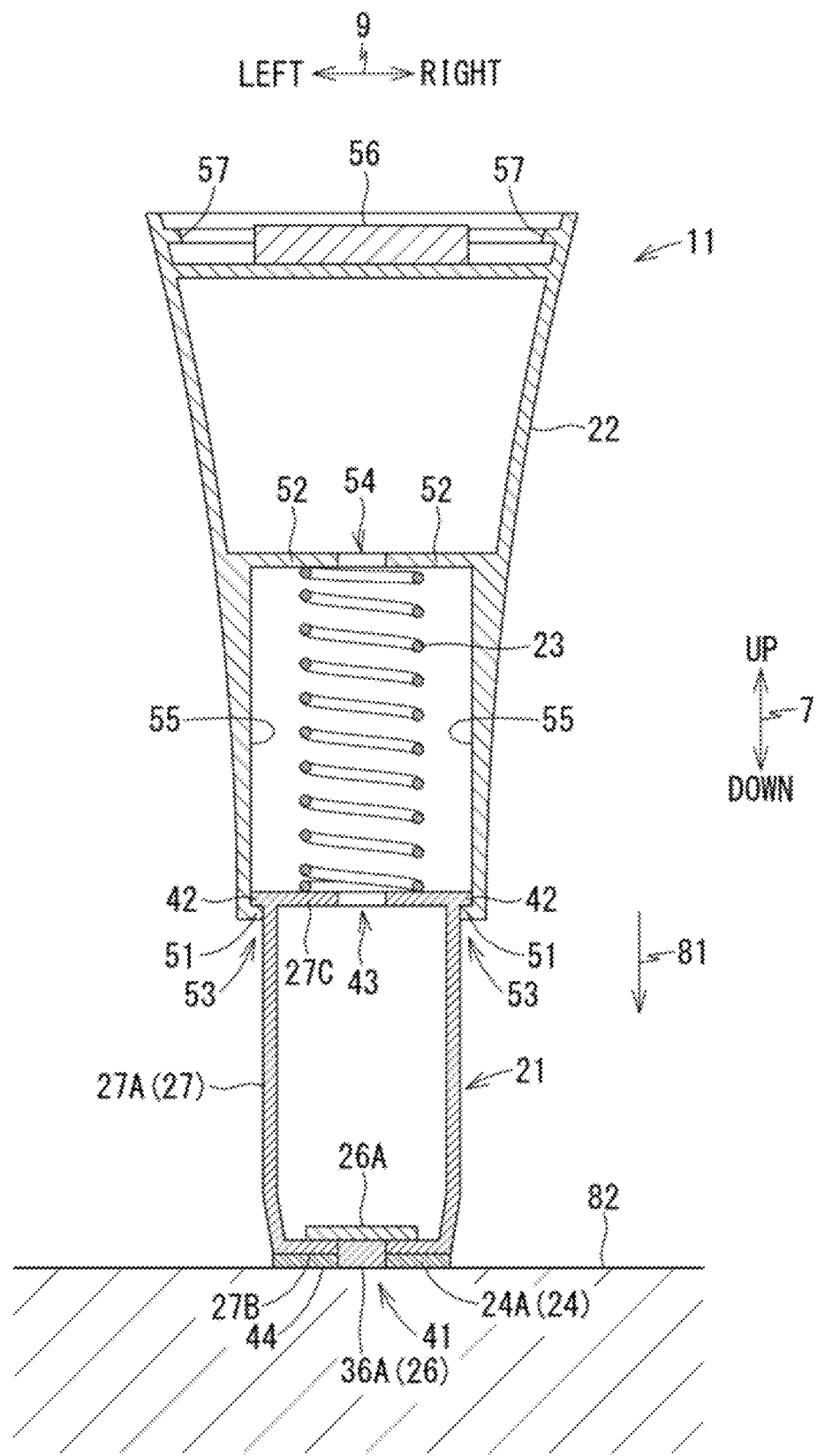
FIG. 3 is a cross-sectional view of the probe portion 11 in no measurement.

As illustrated in FIG. 3, the probe portion 11 has a sensor portion 21, the holding portion 22, a coil spring 23 (example of the transmission portion, the elastic member, and the spring), and a pressure sensor 24.
[Sensor Portion 21]

As illustrated in FIG. 3, the sensor portion 21 has a sensor chip 26 and a sensor housing 27 (example of the housing).
[Sensor Chip 26]

Figure 4:
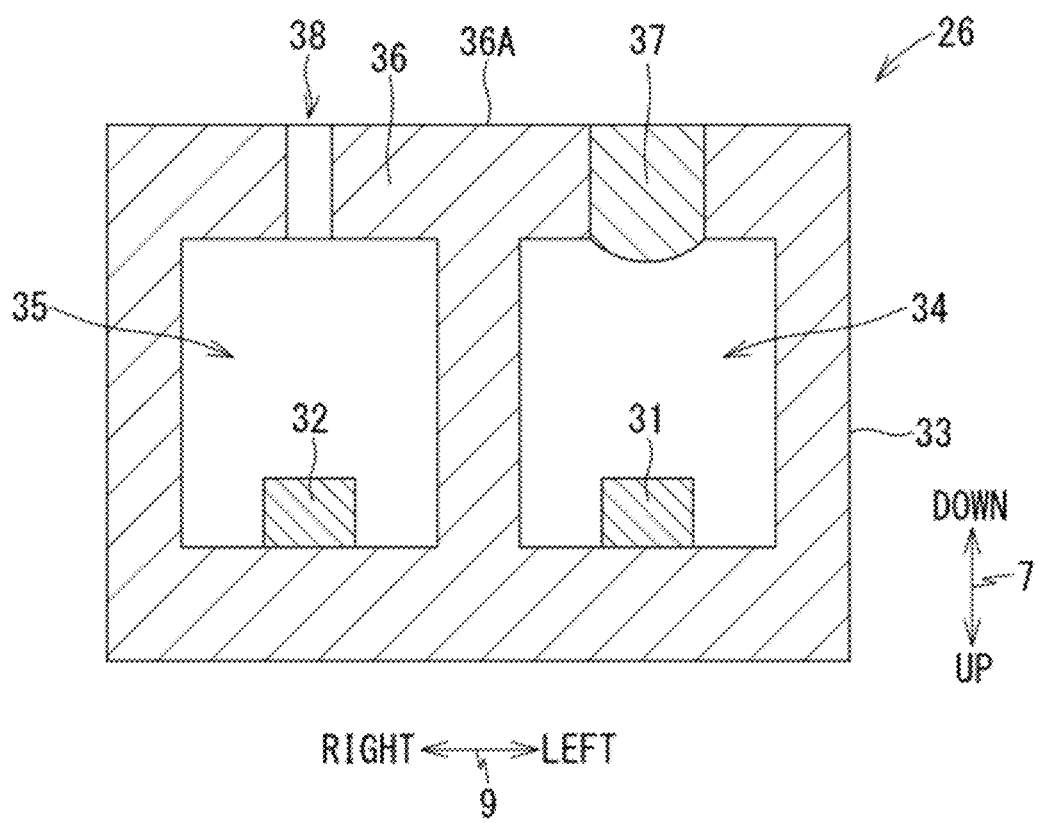
FIG. 4 is a cross-sectional view schematically illustrating a sensor chip 26.

As illustrated in FIG. 4, the sensor chip 26 acquires information on the blood flow volume from a subject in the measurement of the blood flow volume. The sensor chip 26 has a laser diode 31 (example of the laser element, hereinafter sometimes also referred to as "LD"), a photodiode 32 (example of the light receiving element, hereinafter sometimes also referred to as "PD".), and a package 33.

The laser diode 31 outputs laser light by a drive current received through a connector 64 described later from the body portion 12. The photodiode 32 converts received light into an electrical signal, and then outputs the electrical signal. The output electrical signal is transmitted to the body portion 12 through the connector 64.

A package 33 has a substantially rectangular parallelepiped shape with a hollow inside. The inside of the package 33 is divided into two parts. In a LD space 34 of the one part in the package 33, the laser diode 31 is disposed. In a PD space 35 of the other part, the photodiode 32 is disposed.

In a portion adjacent to one side of the LD space 34 of an outer wall 36 of the package 33, a silicon microlens 37 is provided. In a portion adjacent to one side of the PD space 35 of the outer wall 36, a through-hole 38 is provided. Laser light output from the laser diode 31 is output to the outside of the package 33 through the silicon microlens 37. The photodiode 32 receives light entering the PD space 35 from the outside of the package 33 through the through-hole 38.

The sensor chip 26 may have an amplification circuit amplifying the electrical signal output by the photodiode 32.
[Sensor Housing 27]

As illustrated in FIG. 3, the sensor housing 27 holds the sensor chip 26. The sensor housing 27 has a substantially cylindrical shape. The sensor housing 27 has a through-hole 41. The through-hole 41 penetrates the center of a lower wall having a lower surface 27B in the up-and-down direction 7 in the sensor housing 27. Inside the through-hole 41, the sensor chip 26 attached to a substrate 26A, for example, is disposed so that a lower surface 36A is directed downward. The sensor chip 26 or the substrate 26A is stuck to the sensor housing 27 with an adhesive, for example.

The sensor housing 27 has a flange 42. The flange 42 projects outward from an outer peripheral surface 27A of the sensor housing 27 in an upper portion of the sensor housing 27.

The sensor housing 27 has a through-hole 43. The through-hole 43 penetrates the center of an upper wall 27C of the sensor housing 27 in the up-and-down direction 7. An electric cable (not illustrated) electrically connecting the sensor chip 26 and the pressure sensor 24 to a connector 56 described later is inserted into and passed through the through-hole 43.
[Pressure Sensor 24]

The pressure sensor 24 is located on a lower surface 27B of the sensor housing 27. The pressure sensor 24 is a piezoelectric element, for example. A lower surface 24A of the pressure sensor 24 and the lower surface 36A of the sensor chip 26 are located on the same virtual plane. Hereinafter, a surface including the lower surface 24A and the lower surface 36A is referred to as "contact surface 44".
[Holding Portion 22]

The holding portion 22 holds the sensor housing 27. The holding portion 22 has a substantially truncated cone shape. The inside of the holding portion 22 is hollow. The holding portion 22 has extension portions 51 and 52 and holes 53 and 54.

The extension portion 51 extends inward from the lower end of the holding portion 22. The extension portion 52 extends inward from the vicinity of the center in the up-and-down direction 7 in the internal space of the holding portion 22.

The hole 53 is a circular hole demarcated by the tip of the extension portion 51 and communicating with space located above and below the extension portion 51. The sensor housing 27 is inserted into and passed through the hole 53. When the flange 42 of the sensor housing 27 and the extension portion 51 abut on each other, the sensor housing 27 is prevented from being pulled out downward from the holding portion 22.

The holding portion 22 has a guide surface 55 formed ranging over the extension portion 51 and the extension portion 52. The guide surface 55 is an inner peripheral surface of a cylindrical shape. The outer periphery of the flange 42 of the sensor housing 27 is slid with respect to the guide surface 55, whereby the sensor housing 27 is movable in a slide manner in the up-and-down direction 7 with respect to the holding portion 22.

The hole 54 is a circular hole demarcated by the tip of the extension portion 52 and communicating with space located above and below the extension portion 52. The above-described electric cable is inserted into and passed through the hole 54.

The holding portion 22 is provided with the connector 56. The connector 56 is located in a central portion in an upper end portion of the holding portion 22. The connector 56 is electrically connected to the sensor chip 26 and the pressure sensor 24 through the above-described electric cable. In a state where the probe portion 11 is attached to the body portion 12, the connector 56 is brought into electrical connection with a connector 64 (see FIG. 2) described later.

The holding portion 22 has the protrusion portion 57. The protrusion portion 57 projects inward from the inner peripheral surface in an upper portion of the holding portion 22. The protrusion portion 57 is fitted into the recessed portion 69 (see FIG. 2) described later, whereby the probe portion 11 is held in the state of being attached to the body portion.

As illustrated in FIG. 2, the holding portion 22 has the pair of engagement portions 58. The pair of engagement portions 58 is engaged with the engagement portions 65 of the body portion 12 described later, whereby the probe portion 11 is held in the state of being attached to the body portion 12. The pair of engagement portions 58 has a substantially rectangular shape and extends upward from a front portion and a rear portion in the upper end. The pair of engagement portions 58 has the projections 58A projecting inward in the forward and backward direction 8 in an upper end portion.

[Coil Spring 23]

Figure 5:
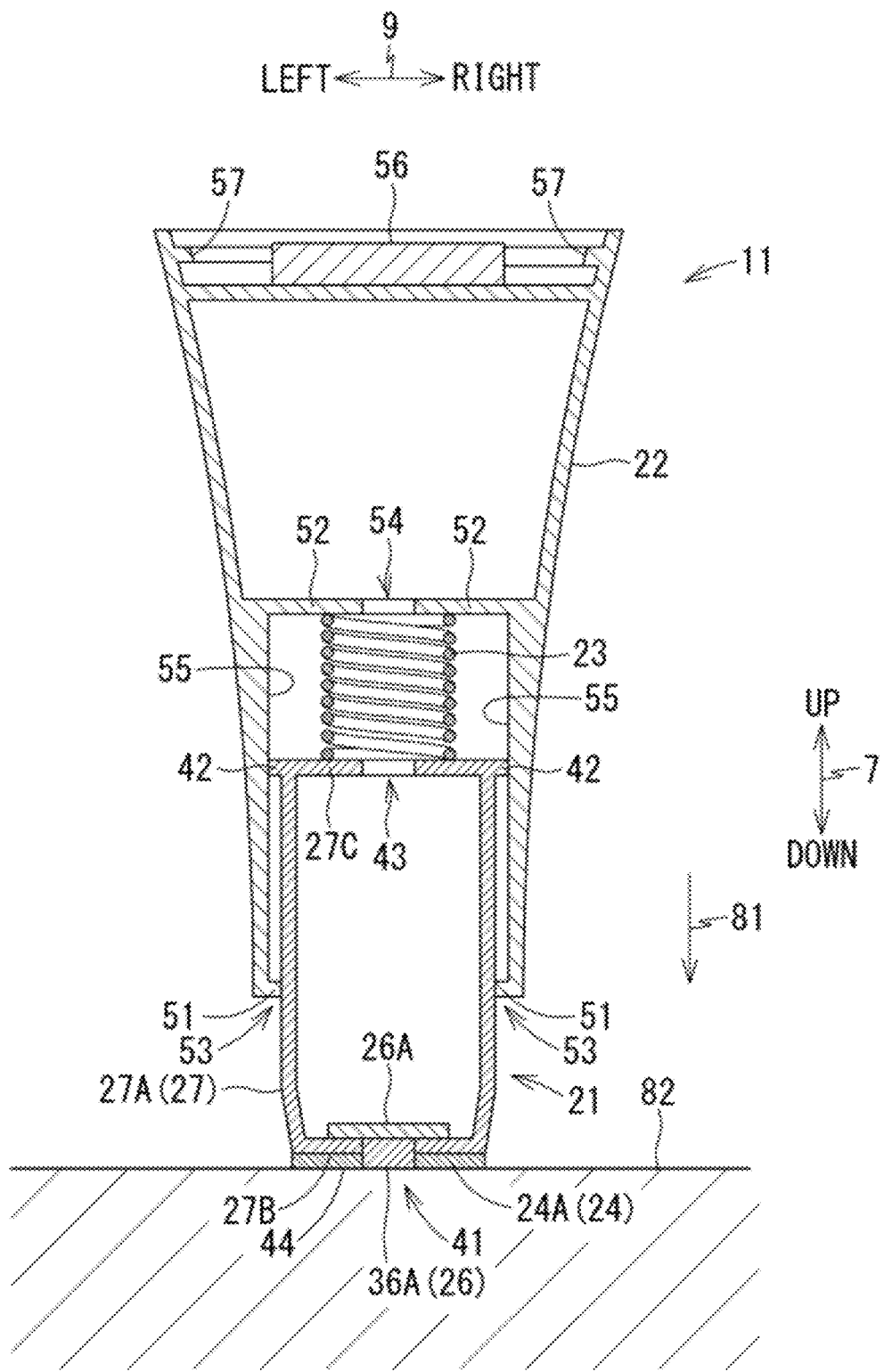
FIG. 5 is a cross-sectional view of the probe portion 11 in measurement.

As illustrated in FIG. 3, the coil spring 23 is disposed in a state of being compressed between the upper wall 27C of the sensor housing 27 and the extension portion 52 of the holding portion 22. As illustrated in FIG. 5, in the state where the holding portion 22 moves in the pressing direction 81 with respect to the sensor housing 27, the coil spring 23 absorbs force transmitted from the holding portion 22 to the sensor housing 27. Therefore, even when the holding portion 22 moves in the pressing direction 81 in the state where a subject 82 contacts the contact surface 44, force (hereinafter referred to as "contact pressure") applied to the subject 82 from the contact surface 44 is hard to fluctuate.

[Body Portion 12]

The body portion 12 calculates the blood flow volume based on the electrical signal relating to the blood flow received from the sensor chip 26, and then displays the blood flow volume on the display portion 62. As illustrated in FIG. 2, the body portion 12 has a body housing 61, the display portion 62, operation portions 63, and the connector 64.

The display portion 62 is a liquid crystal panel, for example. The display portion 62 receives a signal from a control portion 66 described later, and then displays the blood flow volume as a measurement result, for example.

The operation portions 63 are buttons, for example. The operation portions 63 transmit signals to the control portion 66 in response to the pressing of the buttons by a measurement person.

In the state where the probe portion 11 is attached to the body portion 12 (see FIG. 1), the connector 64 is electrically connected to the connector 56 provided in the probe portion 11.

The body housing 61 has the pair of engagement portions 65. When the probe portion 11 is attached to the body portion 12, the pair of engagement portions 65 is engaged with the engagement portions 58 of the probe portion 11. The pair of engagement portions 65 is substantially a rectangular-shaped dent. The pair of engagement portions 65 has recessed portions 65A recessed inward in the forward and backward direction 8 in an upper end portion. The projections 58A in the engagement portions 58 of the probe portion 11 are fitted into the recessed portions 65A of the engagement portions 65, whereby the engagement portions 58 and the engagement portions 65 are engaged with each other.

The body housing 61 has the recessed portion 69 in a lower end portion. The recessed portion 69 is an inward recess from the outer peripheral surface of the body housing 61 and is formed into an endless annular shape. When the probe portion 11 is attached to the body portion 12, the protrusion portion 57 of the probe portion 11 is engaged with the recessed portion 69.

[Cap 13]

As illustrated in FIG. 1, the blood flow measurement device 10 has an attachable and detachable cap 13. In a state of being attached to the blood flow measurement device 10, the cap 13 covers the sensor portion 21.

[Electrical Configuration]

Figure 6:
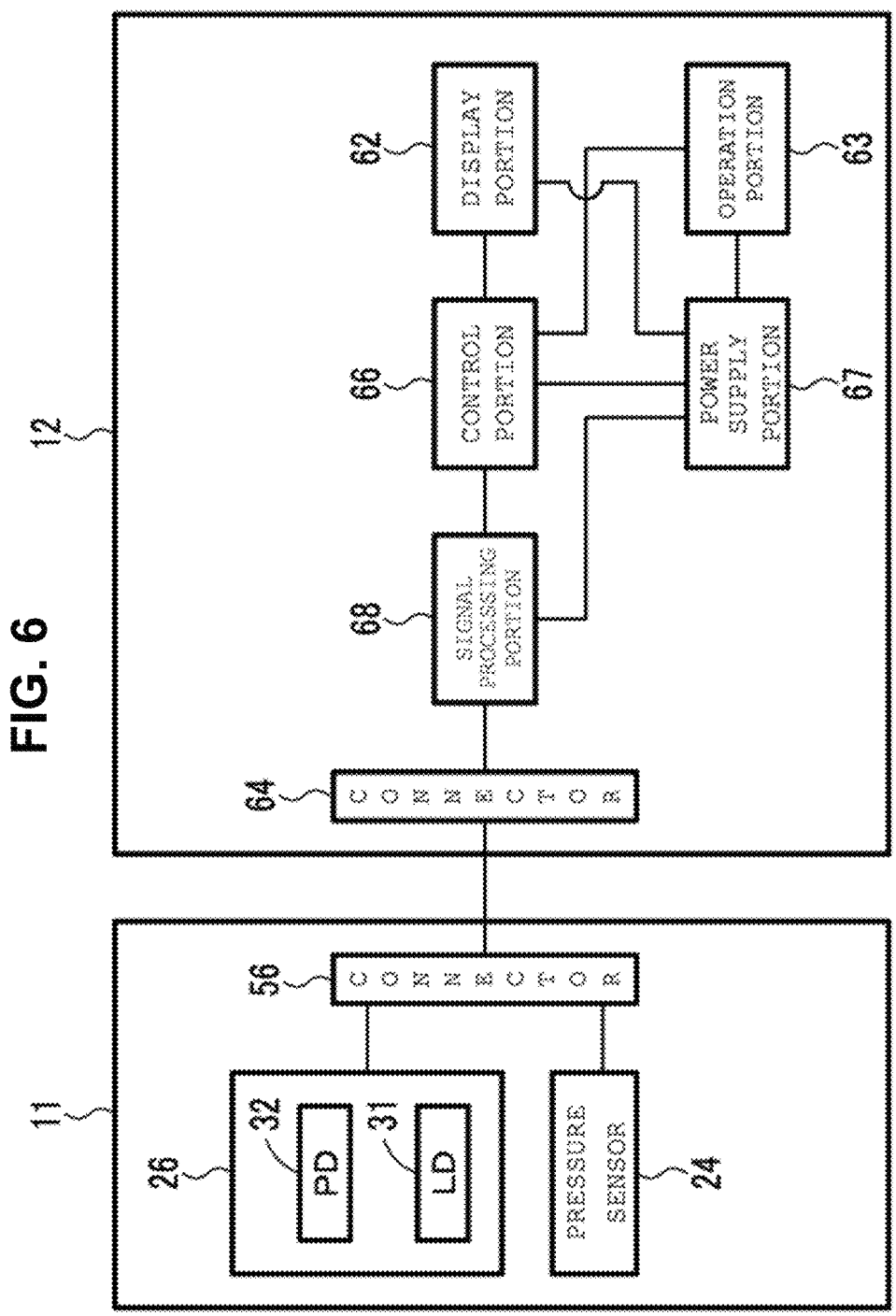
FIG. 6 is a block view illustrating the electrical configuration of the blood flow measurement device 10.

As illustrated in FIG. 6, the body portion 12 further has the control portion 66 (example of the calculation portion), a power supply portion 67, and a signal processing portion 68.

The control portion 66 has a CPU (abbreviation for Central Processing Unit) and a memory. The memory is, for example, a ROM (abbreviation for Read Only Memory), RAM (abbreviation for Random Access Memory), and EEPROM (abbreviation for Electrically Erasable Programmable Read Only Memory).

The CPU receives a digital signal based on an electrical signal output from the photodiode 32 of the sensor chip 26 from the signal processing portion 68, and then performs calculation for calculating the blood flow volume. Moreover, the CPU transmits a signal in order to display a measurement result on the display portion 62, and then receives signals output from the operation portions 63 by the operation of the operation portions 63. The memory stores programs executed by the CPU and data.

The power supply portion 67 is a lithium ion battery, for example. The power supply portion 67 supplies power to the display portion 62 and the signal processing portion 68 based on a direction from the control portion 66.

The signal processing portion 68 is a circuit for signal processing and includes an amplification circuit, an A/D (abbreviation for analog/digital) conversion circuit, and a laser drive circuit, for example.

The signal processing portion 68 outputs a drive current. The drive current is transmitted to the laser diode 31 of the sensor chip 26 through the connectors 56 and 64. Moreover, the signal processing portion 68 amplifies an electrical signal received from the photodiode 32 of the sensor chip 26 through the connectors 56 and 64, and converts the same into a digital signal.

[Calculation of Blood Flow Volume]

Laser is emitted to the subject 82 from the laser diode 31 by the drive current output from the signal processing portion 68. On the other hand, the photodiode 32 receives reflected light of the light emitted from the laser diode 31, converts the received light into an electrical signal, and then outputs the electrical signal. The reflected light received by the photodiode 32 includes scattered light from stationary tissues, such as a blood vessel, and scattered light from moving tissues, such as erythrocytes. The scattered light from the moving tissues have a frequency deviated from the frequency of the scattered light from the stationary tissues by the Doppler shift. Thus, interference occurs in the scattered light from the stationary tissues and the scattered light from the moving tissues and is observed as an optical beat (waviness). Information on the frequency of the optical beat is output from the photodiode 32 as an electrical signal. The control portion 66 calculates the blood flow volume based on the frequency of the optical beat.

[Measurement Processing]

Figure 7:
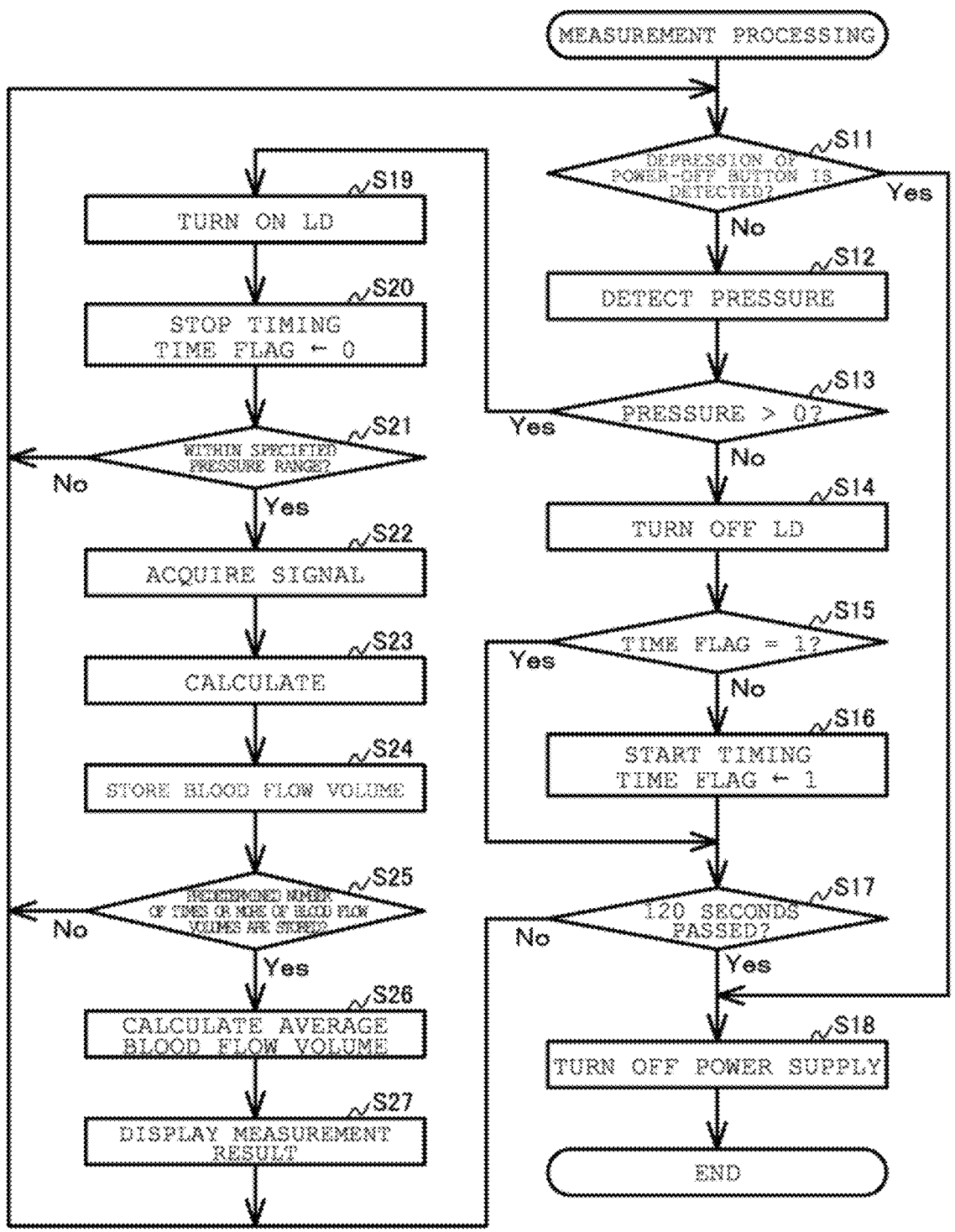
FIG. 7 is a flow chart illustrating the flow of measurement processing.

Measurement processing illustrated in FIG. 7 is processing performed by the control portion 66. The measurement processing is performed based on the fact that a power-ON operation of the operation portion 63 has been performed. The power-ON operation is an operation that a measurement person depresses a button corresponding to power-ON in the operation portion 63, for example.

In the measurement processing, it is judged whether the control portion 66 has detected that a power-OFF operation of the operation portion 63 has been performed, i.e., whether the control portion 66 has received a signal corresponding to the power-OFF operation from the operation portion 63 (Step S11). The power-off operation is an operation that a measurement person depresses a button corresponding to power-OFF, for example. When the control portion 66 has detected that the power-OFF operation of the operation portion 63 has been performed (Step S11: Yes), the control portion 66 transmits a power-OFF signal to the power supply portion 67 to thereby stop the supply of the power to the body portion 12 (Step S18) to complete the measurement processing.

When the control portion 66 has not detected that the power-OFF operation of the operation portions 63 has been performed (Step S11: No), the control portion 66 detects the contact pressure applied to the contact surface 44 based on a signal output by the pressure sensor 24 (Step S12). Then, the control portion 66 judges whether the detected contact pressure is larger than 0 (Step S13). It is judged that the contact surface 44 contacts the subject based on the fact that the contact pressure is larger than 0. The contact pressure for judging that the contact surface 44 contacts the subject may not necessarily be 0 as a reference and a value close to 0 may be previously set, for example.

When the control portion 66 does not judge that the contact pressure is larger than 0 (Step S13: No), the control portion 66 transmits a laser-off signal to the signal processing portion 68 to thereby cause the signal processing portion 68 to stop the supply of the drive current to the laser diode 31 (Step S14). Then, the control portion 66 judges whether 1 is stored in a time flag stored in the memory (Step S15).

When the control portion 66 judges that 1 is not stored in the time flag (Step S15: No), the control portion 66 starts timing and stores 1 in the time flag stored in the memory (Step S16) to proceed the process to Step S17. When the control portion 66 judges that 1 is stored in the time flag (Step S15: Yes), the control portion 66 skips the processing of Step S16, and then proceeds the process to Step S17.

In Step S17, the control portion 66 judges whether a predetermined time stored in the memory, for example, 120 seconds, has passed after starting the timing. When the control portion 66 has judged that 120 seconds have passed after starting the timing (Step S17: Yes), the control portion 66 transmits a power-OFF signal to the power supply portion 67 to thereby stop the supply of the power to the body portion 12 (Step S18) to complete the measurement processing.

On the other hand, when the control portion 66 does not judge that 120 seconds have passed after starting the timing (Step S17: No), the control portion 66 returns the process to the processing of Step S11, and then judges whether a power-OFF operation of the operation portions 63 has been performed based on signals input from the operation portions 63.

When the control portion 66 has judged that the contact pressure is larger than 0 (Step S13: Yes), the control portion 66 transmits a laser-on signal to the signal processing portion 68 to thereby cause the signal processing portion 68 to start the supply of a drive current to the laser diode 31 (Step S19).

Moreover, the control portion 66 stops the timing and stores 0 in the time flag stored in the memory (Step S20). When timing is not performed and 0 is stored in the time flag, the control portion 66 may not perform this step.

Then, the control portion 66 judges whether the contact pressure detected in Step S12 is within a predetermined specified pressure range previously stored in the memory (Step S21). The specified pressure range is previously set as the range of the contact pressure where the blood flow measurement is stably performed. When the control portion 66 has judged that the contact pressure detected in Step S12 is within the specified pressure range (Step S21: Yes), the control portion 66 acquires a digital signal output from the signal processing portion 68 (Step S22). Then, the control portion 66 calculates the blood flow volume based on the acquired digital signal (Step S23), and then stores the calculated blood flow volume in the memory (Step S24). The processing of Step S22 and the processing of Step S23 are examples of the calculation.

The processing of Step S22, the processing of Step S23, and the processing of Step S24 are performed at predetermined time intervals previously stored in the memory, for example, 5 seconds. Thus, a plurality of blood flow volumes with time intervals is acquired. The blood flow volume to be stored is added and stored without overwriting the previously stored blood flow volume. Therefore, when the measurement is continued, the plurality of blood flow volumes is stored in the memory. The number of the blood flow volumes stored in the memory may be counted by counting up a counter whenever the blood flow volume is stored in the memory.

Then, the control portion 66 judges whether the predetermined number, e.g., five or more, of blood flow volumes previously stored in the memory are stored in the memory (Step S25). When the control portion 66 judges that the predetermined number or more of the blood flow volumes are stored in the memory (Step S25: Yes), the control portion 66 calculates an average value of the blood flow volumes stored in the memory (Step S26). Then, the control portion 66 displays the calculated average value as a measurement result of blood flow volume on the display portion 62 (Step S27).

In the case where the control portion 66 judges that the contact pressure detected in Step S12 is not within the specified pressure range in Step S21 (Step S21: No), when the blood flow volume is already stored in the memory in Step S24, the control portion 66 erases the blood flow volume from the memory, and then returns the process to the processing of Step S11. Then, the control portion 66 judges whether the control portion 66 has detected that a power-OFF operation of the operation portions 63 has been performed based on signals input from the operation portions 63.

Operational Effects of First Embodiment

As described above, the blood flow volume is measured in the state where the contact surface 44 of the sensor housing 27 is brought into contact with the subject 82 (for example, skin of a human body). The sensor housing 27 is movably held in the holding portion 22. External force (for example, force applied to the blood flow measurement device 10 by a measurement person) applied to the holding portion 22 is absorbed and transmitted to the sensor housing 27 by the coil spring 23. Therefore, when the external force is applied to the holding portion 22, changes of the contact pressure of the contact surface 44 to the subject 82 (skin) are suppressed. Thus, a fluctuation of the blood flow volume of the subject 82 during the measurement is suppressed.

The control portion 66 stops the calculation of calculating the blood flow volume according to the fact that the contact pressure detected by the pressure sensor 24 is not within the predetermined range, and therefore the display of measurement results with low reliability on the display portion 62 is avoided.

The control portion 66 starts the calculation of calculating the blood flow volume according to the fact that the pressure has been detected by the pressure sensor 24, and therefore even when the pressure detected by the pressure sensor 24 is out of the predetermined range, the calculation is resumed without explicit giving of a direction of starting the measurement to the control portion 66 by a measurement person.

The control portion 66 performs the calculation of calculating the blood flow volume by a plurality of times, and then calculates an average value of results of the plurality of times of the calculations. Then, the average value is displayed as a measurement result on the display portion 62. Therefore, a more reliable measurement result is displayed.

Second Embodiment

In a second embodiment, a probe portion 15 (example of the blood flow sensor) is used in place of the probe portion 11 in the blood flow measurement device 10 of the first embodiment. The other configurations are the same as those of the first embodiment. The probe portion 15 is attachable to and detachable from the body portion 12 as with the probe portion 11.

Figure 8:
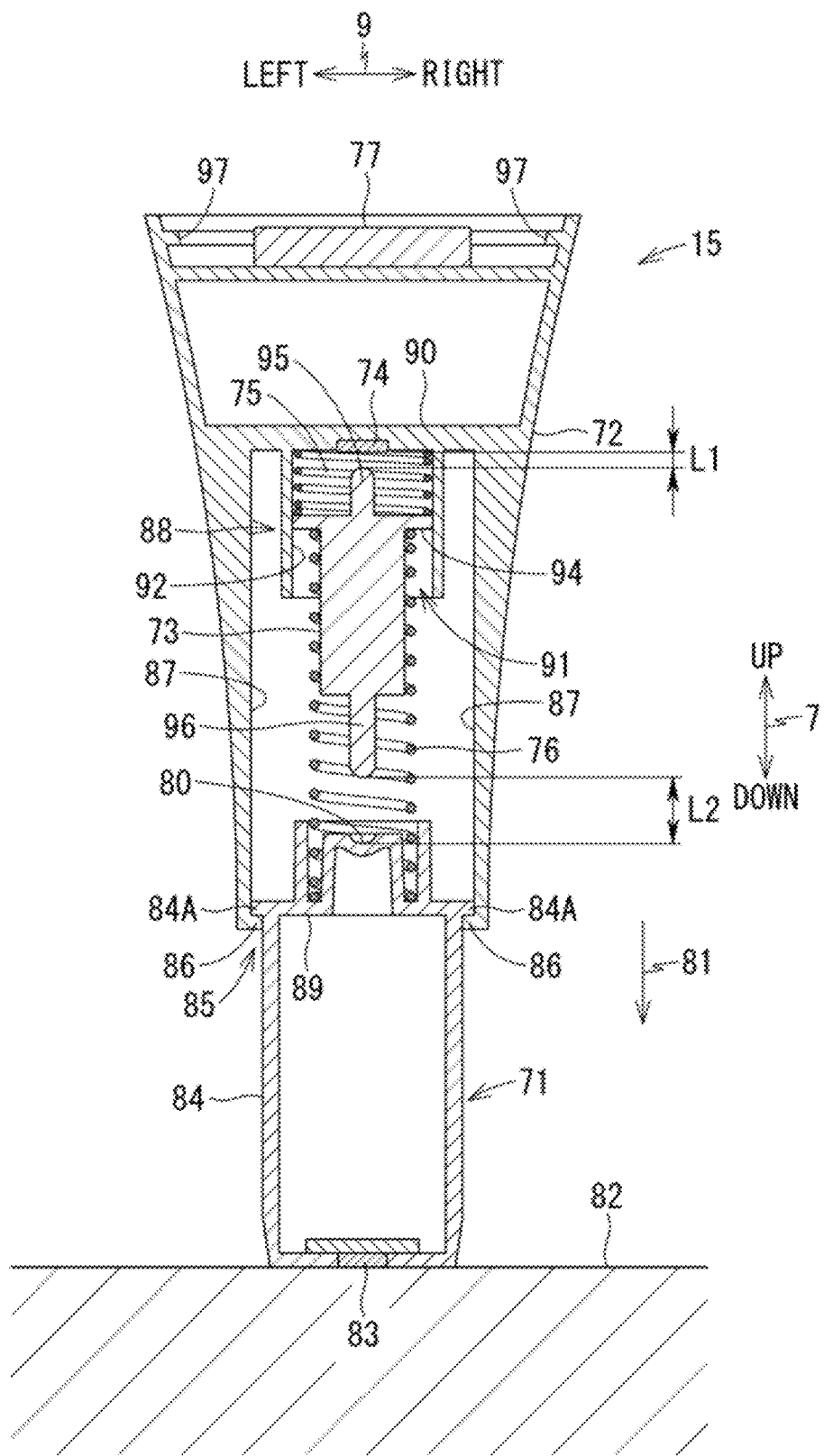
FIG. 8 is a cross-sectional view of a probe portion 15 according to a second embodiment.

As illustrated in FIG. 8, the probe portion 15 has an optical sensor portion 71, a holding portion 72, a moving member 73, a pressure sensor 74, and coil springs 75 and 76.

[Optical Sensor Portion 71]

The optical sensor portion 71 has a sensor chip 83 and a sensor housing 84 (example of the housing) similar to the sensor portion 21 according to the first embodiment, and therefore a detailed explanation is omitted herein. The optical sensor portion 71 is not provided with a pressure sensor.

[Holding Portion 72]

The holding portion 72 holds the optical sensor portion 71 so as to be movable in the up-and-down direction 7. The outer shape of the holding portion 72 is a substantially truncated cone shape. The inside of the holding portion 72 is space where a part of the optical sensor portion 71 and the moving member 73, the pressure sensor 74, and the coil springs 75 and 76 can be accommodated.

In the lower end of the outer wall forming the outer shape of the holding portion 72, an opening 85 is formed. The inner diameter of the opening 85 is equivalent to the outer diameter in the vicinity of the center in the up-and-down direction 7 of the sensor housing 84. The opening 85 is opened along the up-and-down direction 7. The optical sensor portion 71 is inserted into the opening 85. A flange 84A extending outward is formed in the upper end of the sensor housing 84. The outer shape of the flange 84A is larger than the inner diameter of the opening 85. The flange 84A can abut on a peripheral portion 86 demarcating the opening 85 from above. Due to the fact that the flange 84A abuts on the peripheral portion 86, the moving lower end (position illustrated in FIG. 8) of the optical sensor portion 71 moving in the up-and-down direction 7 with respect to the opening 85 is determined.

In the internal space of the holding portion 72, an inner peripheral surface 87 of a cylindrical shape extends upward from the peripheral portion 86. The inner diameter of the inner peripheral surface 87 is constant in the up-and-down direction 7 and is equivalent to the outer shape of the peripheral portion 86. When the sensor housing 84 moves in the up-and-down direction 7 with respect to the opening 85, the peripheral portion 86 is guided by the inner peripheral surface 87 to slide with respect to the inner peripheral surface 87.

In the vicinity of an upper portion of the inner peripheral surface 87, a guide tube 88 is formed. The guide tube 88 has a cylindrical shape with an outer diameter smaller than the inner diameter of the inner peripheral surface 87. An upper wall 90 expanding outward is formed on the upper end of the guide tube 88. The upper wall 90 is continuous to the outer wall of the holding portion 72. The upper end of the guide tube 88 is blocked with the upper wall 90. In the lower end of the guide tube 88, an opening 91 is formed. The inner peripheral surface 92 of the guide tube 88 guides the moving member 73 in the up-and-down direction 7.

[Moving Member 73]

The moving member 73 has a disk portion 94, a first projection 95 projecting upward from the disk portion 94, and a second projection 96 projecting downward from the disk portion 94. The disk portion 94 has a disk shape with an outer diameter equivalent to the inner diameter of the inner peripheral surface 92 of the guide tube 88. The disk portion 94 is accommodated in the internal space of the guide tube 88 with an attitude that flat upper and lower surfaces are individually directed in the up-and-down direction 7 and is movable in the up-and-down direction 7 while the outer peripheral surface is sliding on the inner peripheral surface 92. The first projection 95 projects upward from the center of the disk portion 94. The length of the first projection 95 projecting upward from the disk portion 94 is shorter than the length along the up-and-down direction 7 of the guide tube 88. The second projection 96 projects downward from the center of the disk portion 94. The length of the second projection 96 projecting downward from the disk portion 94 is shorter than the length along the up-and-down direction 7 from the upper wall 90 of the guide tube 88 to the peripheral portion 86. The length along the up-and-down direction 7 of the moving member 73 is longer than the length along the up-and-down direction 7 of the guide tube 88. The second projection 96 can abut on a recessed portion 80 formed in the center of the upper wall 89 of the sensor housing 84 of the optical sensor portion 71.

[Pressure Sensor 74]

A pressure sensor 74 is provided on the lower surface of the upper wall 90 of the guide tube 88. The pressure sensor 74 is a pressure sensitive sensor, such as a piezoelectric element, for example. In the pressure sensor 74, the lower surface is a pressure sensitive surface and outputs an electrical signal according to the magnitude of the force given to the lower surface. On the lower surface of the pressure sensor 74, the first projection 95 of the moving member 73 can abut.

[Coil Springs 75 and 76]

Figure 9:
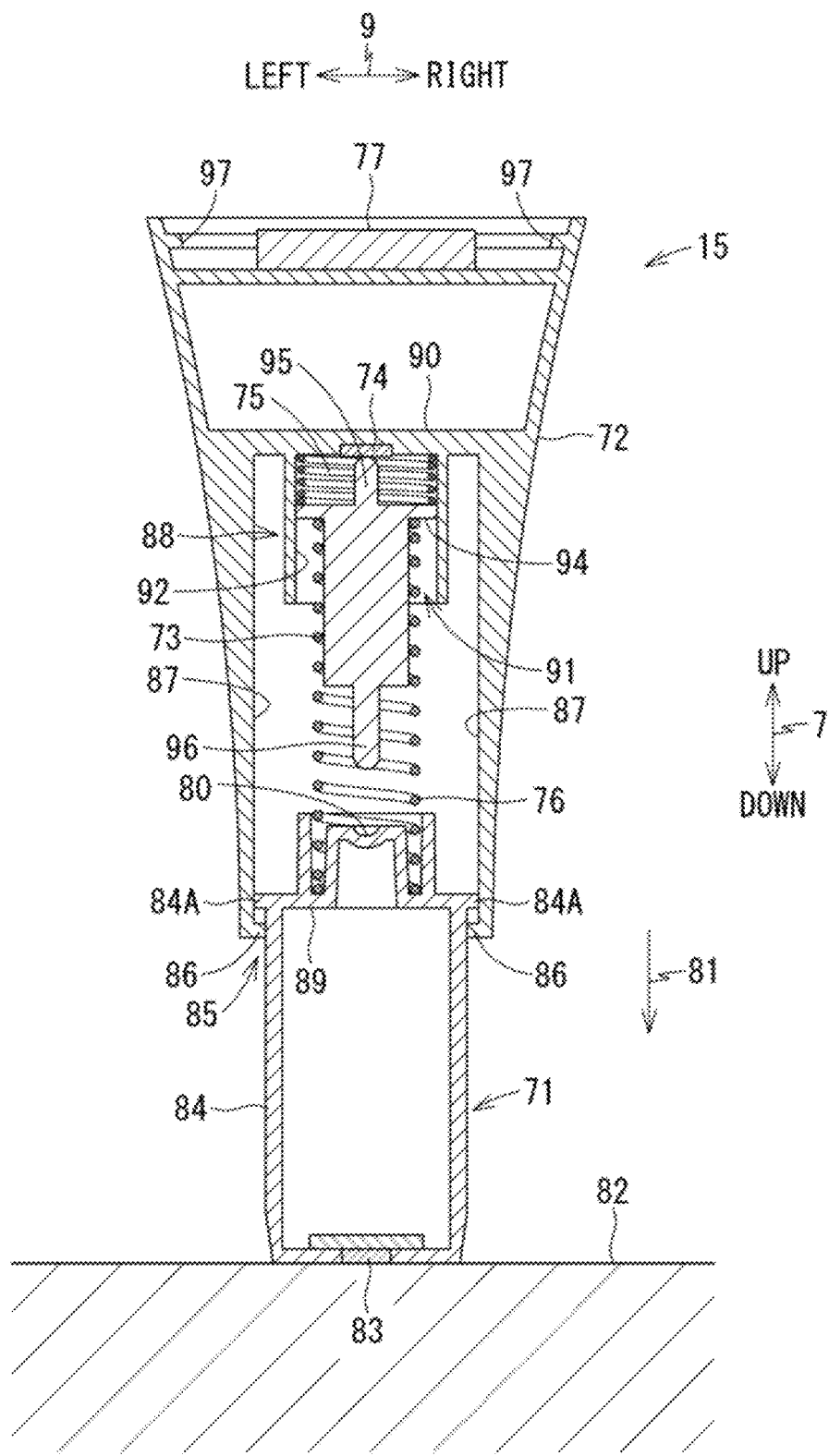
FIG. 9 is a cross-sectional view of the probe portion 15 in measurement.

The coil spring 75 (example of the first elastic body) is located between the moving member 73 and the pressure sensor 74 with the disk portion 94 of the moving member 73 and the upper wall 90 of the guide tube 88 as spring seats. The moving member 73 is energized downward (example of the first direction) in FIG. 8 by the coil spring 75. The coil spring 75 can be elastically compressed and deformed in the up-and-down direction 7. Due to the fact that the moving member 73 moves upward (example of the second direction) in FIG. 8 against the energization force of the coil spring 75, the first projection 95 of the moving member 73 abuts on the pressure sensor 74 (see FIG. 9).

Figure 10:
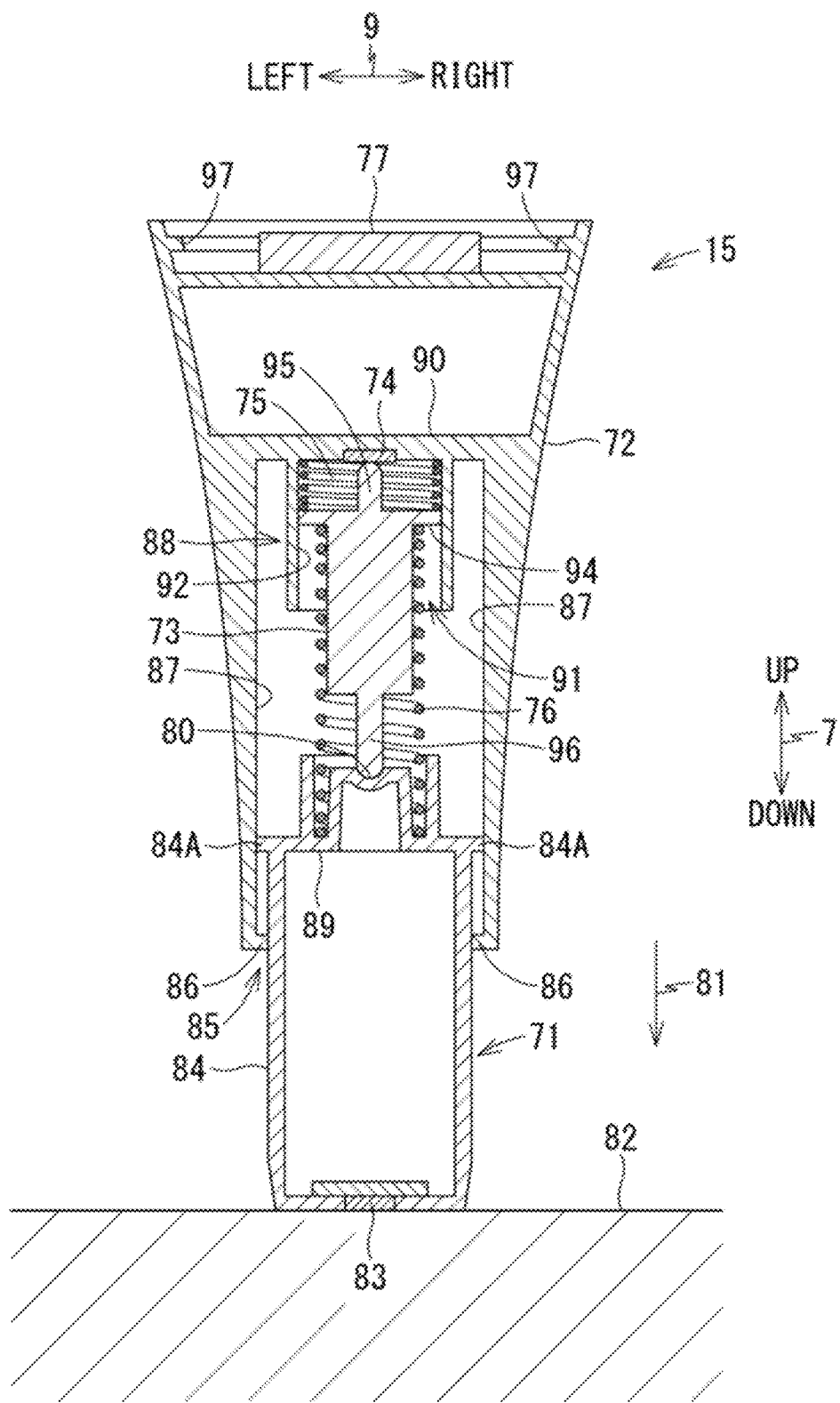
FIG. 10 is a cross-sectional view of the probe portion 11 in a state where an excessive load is given.

The coil spring 76 (example of the second elastic body) is located between the disk portion 94 of the moving member 73 and a spring seat 93 which is formed on the upper surface of the sensor housing 84 of the optical sensor portion 71 and is recessed downward. The optical sensor portion 71 is energized downward in FIG. 8 by the coil springs 75 and 76. The coil spring 76 can be elastically compressed and deformed in the up-and-down direction 7. Due to the fact that the optical sensor portion 71 moves upward in FIG. 8 against the energization force of the coil spring 76, the second projection 96 of the moving member 73 abuts on the recessed portion 80 of the optical sensor portion (see FIG. 10).

First energization force F1 of the coil spring 75 in a state where the first projection 95 of the moving member 73 and the pressure sensor 74 abut on each other (see FIG. 9) is lower than second energization force F2 of the coil spring 76 in a state where the second projection 96 of the moving member 73 and the recessed portion 80 of the optical sensor portion 71 abut on each other (see FIG. 10) (F1<F2). Therefore, the coil spring 75 is more easily compressed and deformed than the coil spring 76.

As illustrated in FIG. 8, in the equilibrium in which the energization force of the coil spring 75 and the energization force of the coil spring 76 are balanced, the first projection 95 does not abut on the pressure sensor 74 and the second projection 96 does not abut on the recessed portion 80 in the moving member 73. In this equilibrium, a first distance L1 along the up-and-down direction 7 (movement direction) between the upper end of the first projection 95 of the moving member 73 and the pressure sensor 74 is shorter than a second distance L2 along the up-and-down direction 7 between the recessed portion 80 of the optical sensor portion 71 and the lower end of the second projection 96 of the moving member 73 (L1<L2).

In the vicinity of the upper end of the holding portion 72, a connector 77 is provided. The connector 77 is electrically connected to the sensor chip 83 and the pressure sensor 74 through an electric cable. When the probe portion 15 is connected to the body portion 12, the connector 77 is electrically connected to the connector 64 (see FIG. 2).

In the vicinity of the upper end of the inner peripheral surface of the holding portion 72, a protrusion portion 97 projecting inwardly is formed. The protrusion portion 97 is fitted into the recessed portion 69 (see FIG. 2), whereby the probe portion 15 is attached to the body portion 12.

[Measurement Processing]

Measurement processing using the probe portion 15 is performed by the control portion 66 (example of the calculation portion). In a memory (example of the storage portion) of the calculation portion 66, a first threshold value and a second threshold value are previously stored. The first threshold value is a value which is expected to be output from the pressure sensor 74 when the coil spring 75 is compressed and deformed, so that the first projection 95 of the moving member 73 abuts on the pressure sensor 74. The second threshold value is a value which is expected to be output from the pressure sensor 74 when the coil springs 75 and 76 are compressed and deformed, so that the first projection 95 of the moving member 73 abuts on the pressure sensor 74 and the second projection 96 of the moving member 73 abuts on the recessed portion 80 of the optical sensor portion 71.

The measurement processing using the probe portion 15 is the same as the measurement processing in the first embodiment. More specifically, when the control portion 66 does not detect that a power-OFF operation of the operation portions 63 has been performed (FIG. 7, step S11: No), the control portion 66 calculates pressure based on a signal output by the pressure sensor 74 (FIG. 7, Step S12). Then, the control portion 66 judges whether the calculated pressure is higher than the first threshold value (FIG. 7, Step S13). It is judged that the optical sensor portion 71 contacts the subject based on the fact that the contact pressure is higher than the first threshold value. The electric strength of signals, such as a voltage, may be compared with the first threshold value without calculating pressure based on a signal output by the pressure sensor 74.

Moreover, the control portion 66 judges whether the pressure detected in Step S12 is within a predetermined specified pressure range, i.e., between the first threshold value and the second threshold value, previously stored in the memory (FIG. 7, Step S21). In a case where the control portion 66 has judged that the pressure detected in Step S12 is not within the specified pressure range in Step S21 (FIG. 7, Step S21: No), when the blood flow volume is already stored in the memory in Step S24, the control portion 66 erases the blood flow volume from the memory, and then returns the process to the processing of Step S11. Moreover, the control portion 66 displays a display warning that the pressure applied to the optical sensor portion 71 is out of the fixed range on the display portion 62 (example of the warning portion).

Operational Effects of Second Embodiment

According to the probe portion 15 of the second embodiment, when the contact surface of the optical sensor portion 71 contacts a subject in the state where the holding portion 72 is directly or indirectly held by a user, the moving member 73 moves upward, so that the first projection 95 abuts on the pressure sensor 74. The calculation portion 66 receives a signal output from the pressure sensor 74 by the abutment of the first projection 95, and then calculates the blood flow volume based on the output of the optical sensor portion 71.

When the contact surface of the optical sensor portion 71 is brought into contact with a subject in the state where the holding portion 72 is directly or indirectly held by a user, the coil spring 75 is compressed and deformed, so that the first projection 95 and the pressure sensor 74 abut on each other.

Furthermore, when the contact surface of the optical sensor portion 71 is strongly pressed against a subject, the coil spring 76 is compressed and deformed, so that the recessed portion 80 and the second projection 96 abut on each other. Thus, the force applied to the optical sensor portion 71 is directly transmitted to the pressure sensor 74 without being absorbed by the coil springs 75 and 76.

The first projection 95 of the moving member 73 and the pressure sensor 74 abut on each other with a relatively short distance. Moreover, the distance until the recessed portion 80 of the optical sensor portion 71 and the second projection 96 of the moving member 73 abut on each other in the state where the first projection 95 and the pressure sensor 74 abut on each other is relatively long, and therefore a relative distance between the recessed portion 80 of the optical sensor portion 71 and the second projection 96 of the moving member 73 where the blood flow volume can be measured is long.

Moreover, when a proper load exceeding the first threshold value is given to the contact surface of the optical sensor portion 71, the calculation portion 66 calculates the blood flow volume. When an excessive load exceeding the second threshold value is given to the contact surface of the optical sensor portion 71, a warning is issued.

[Other Modifications]

In the embodiments described above, the coil springs 23, 75, and 76 are used as examples of the transmission portion, the other members may be used in place of the coil springs 23, 75, and 76 insofar as the members can absorb and transmit external force applied to the holding portions 22 and 72 to the sensor housings 27 and 84. For example, elastic bodies, such as a sponge, a porous elastic body, and a gel elastic body, dampers containing air or liquid thereinside, and dampers using repulsive force, such as electromagnetic force, may be used in places of the coil springs 23, 75, and 76.

The contact surface 44 does not necessarily need to be a plane and the contact surface 44 may be a projected curved surface, for example.

The power supply portion 67 does not necessarily need to be a lithium ion battery and may be another secondary battery or may be a primary battery. Moreover, a commercial power supply may be used.

The blood flow measurement device 10 may be provided with a sending portion capable of sending data to information processing devices, such as a PC (abbreviation for a personal computer).

Moreover, the warning that the pressure applied to the optical sensor portion 71 is out of the specified range may be issued with a buzzer sound, an LED lamp, or the like, for example, in place of the display by the display portion 62.

REFERENCE SIGNS LIST

7 . . . up-and-down direction
8 . . . forward and backward direction
9 . . . left and right direction
10 . . . blood flow measurement device
11, 15 . . . probe portion (blood flow sensor)
21 . . . sensor portion
22, 72 . . . holding portion
23, 75, 76 . . . coil spring (transmission portion, elastic member, spring)
24 . . . pressure sensor
26 . . . sensor chip
27, 84 . . . sensor housing (housing)
31 . . . laser diode (laser element)
32 . . . photodiode (light receiving element)
44 . . . contact surface
62 . . . display portion
66 . . . control portion (calculation portion)
71 . . . optical sensor portion
73 . . . moving member
81 . . . pressing direction (direction crossing contact surface)
82 . . . subject

The invention claimed is:

1. A blood flow sensor comprising:
an optical sensor portion having a laser element for generating laser light, a light receiving element for receiving reflected light, and a housing having a contact surface for contacting a subject, the laser element for irradiating the subject with the laser light through the contact surface, the light receiving element for receiving said reflected light from the subject and then outputting a first signal relating to a received light amount;
a holding portion holding the housing and configured to be movable relative to the housing in movement directions toward and away from the contact surface of the housing;
a first non-electromagnetic elastic member located within the holding portion biasing the optical sensor portion in a first direction away from the holding portion;
a second non-electromagnetic elastic member located within the holding portion distal to the first non-electromagnetic member;
a moving member located within the holding portion and being biased in the first direction by the first non-electromagnetic elastic member, the moving member having a first projection, a second projection, and a first section between the first projection and second projection, the first section located between the first non-electromagnetic member and the second non-electromagnetic member; and
a pressure sensor situated within the holding portion proximal to the first projection, the pressure sensor detecting pressure from contact with the first projection when the moving member is moved in a second direction opposite the first direction in response to an external force applied to the blood flow sensor acting upon the first non-electromagnetic elastic member and the second non-electromagnetic elastic member, the pressure sensor outputting a second signal in response to said pressure from said contact by the first projection; and
wherein the blood flow sensor has an equilibrium state in which there is no external force acting upon the first non-electromagnetic elastic member and the second non-electromagnetic elastic member, and in said equilibrium state the first projection is spaced apart from the pressures sensor by a first distance and the second projection is spaced apart from the optical sensor portion by a second distance.

2. The blood flow sensor according to claim 1 wherein when said external force exceeds a first threshold the moving member is moved to have the first projection in contact with the pressure sensor, when said external force exceeds a second threshold greater than the first threshold a seat of the optical sensor portion is in contact with the second projection, and when said external force is greater than the first threshold and less than the second threshold the seat of the optical sensor portion is out of contact with the second projection.

3. The blood flow sensor according to claim 1, wherein while the blood flow sensor is in said equilibrium state, said second distance exceeds said first distance.

4. A blood flow volume measuring device comprising:
the blood flow sensor according to claim 2;
a calculation portion calculating a blood flow volume based on the first signal and the second signal;
a storage portion storing a first threshold value and a second threshold value; and
a warning portion issuing a warning, wherein
the calculation portion calculates the blood flow volume based on the first signal when the second signal corresponds to pressure detected by the pressure sensor for said external force which causes the first projection to be in contact with the pressure sensor while the second projection spaced apart from said seat of the optical sensor portion; and
wherein the calculation portion causes the warning portion to issue a warning when the second signal corresponds to pressure detected by the pressure sensor for said external force which causes said seat of the optical sensor portion to be in contact with the second projection.

5. A blood flow volume measuring device comprising:
the blood flow sensor according to claim 2;
a calculation portion calculating a blood flow volume based on the first signal and the second signal;
a display portion for displaying a blood flow measure derived by the calculation portion; and
a storage portion for storing a plurality of predetermined timings as a range of timings from a first timing to a last timing and for storing an indication of a predetermined pressure range corresponding to an external force between said first threshold and said second threshold;

wherein when the calculation portion acquires a pressure reading detected by the pressure sensor at a given timing among said plurality of predetermined timings and the first projection is in contact with the pressure sensor, then the calculation portion performs a first calculation for said given timing;

wherein when the calculation portion acquires the pressure reading detected by the pressure sensor at the given timing among said plurality of predetermined timings and the second projection is in contact with the optical sensor portion, then the calculation portion stops performing the first calculation for the given timing and later timings among the range of timings from the first timing to the last timing and deletes current results of the first calculation for each timing among the range of timings from the first timing to the last timing for which the first calculation was performed; and wherein when the calculation portion performs the first calculation for each one timing among said plurality of predetermined timings, the calculation portion calculates said blood flow measure from said current results of said first calculation for each one timing among said plurality of predetermined timings and displays said calculated blood flow measure.

\* \* \* \* \*